US00PP19761P2

(12) United States Plant Patent
Meinl

(10) Patent No.: US PP19,761 P2
(45) Date of Patent: Feb. 24, 2009

(54) **VARIETY OF *HYDRANGEA* PLANT NAMED 'HORPILL'**

(50) Latin Name: *Hydrangea macrophylla*
Varietal Denomination: Horpill

(75) Inventor: Katrin Meinl, Dresden (DE)

(73) Assignee: Claus & Torsten Kühne GbR, Dresden (DE)

( * ) Notice: Subject to any disclaimer, the term of this patent is extended or adjusted under 35 U.S.C. 154(b) by 0 days.

(21) Appl. No.: 11/978,306

(22) Filed: Oct. 29, 2007

(51) Int. Cl.
*A01H 5/00* (2006.01)

(52) U.S. Cl. ..... Plt./250
(58) Field of Classification Search ..... Plt./250
See application file for complete search history.

*Primary Examiner*—Kent L Bell
(74) *Attorney, Agent, or Firm*—The Webb Law Firm

(57) ABSTRACT

A new and distinct bicoloured *Hydrangea* plant having dark foliage and a compact growth habit.

1 Drawing Sheet

Botanical classification: *Hydrangea macrophylla* hybrid.
Varietal denomination: 'HORPILL'.

BACKGROUND OF THE INVENTION

The present invention comprises a new and distinct cultivar of *Hydrangea* plant known by the varietal name 'Horpill'. The new variety was discovered in 1999 in a planned breeding program in Dresden, Germany. The purpose of the breeding program was to develop bicoloured *Hydrangeas*. The new variety is the result of a cross between 'Moritzburg' (female parent, unpatented) and 'Nobuko' (male parent). The inflorescence shape and foliage of the new variety are similar to its female parent, but 'Moritzburg' is not bicoloured. 'Nobuko' is bicoloured like the new variety, but differs from 'Horpill' in growth habit. The new variety was first asexually reproduced in 1999 via propagation by cuttings in Germany. The new variety has been trial and field tested in Germany and has been found to retain its distinctive characteristics and remain true to type through successive propagations.

The following traits distinguish 'Horpill' as a new and distinct cultivar from other *Hydrangea* varieties known to the breeder:

1. Bicoloured in nature;
2. Strong stems;
3. Dark foliage;
4. Compact growth habit;
5. Small leaves; and
6. Good root system.

'Horpill' is similar to another *Hydrangea* variety, 'Harlekin' (unpatented), because they are both bicoloured with mop-heads and a compact growth habit. However, 'Horpill' differs from 'Harlekin' in stem quality, sterile flower shape, and root system characteristics.

DESCRIPTION OF THE DRAWING

The accompanying photographic drawing illustrates the new variety, with the color being as nearly true as is possible with color illustrations of this type.

DESCRIPTION OF THE PLANT

Figure 1:
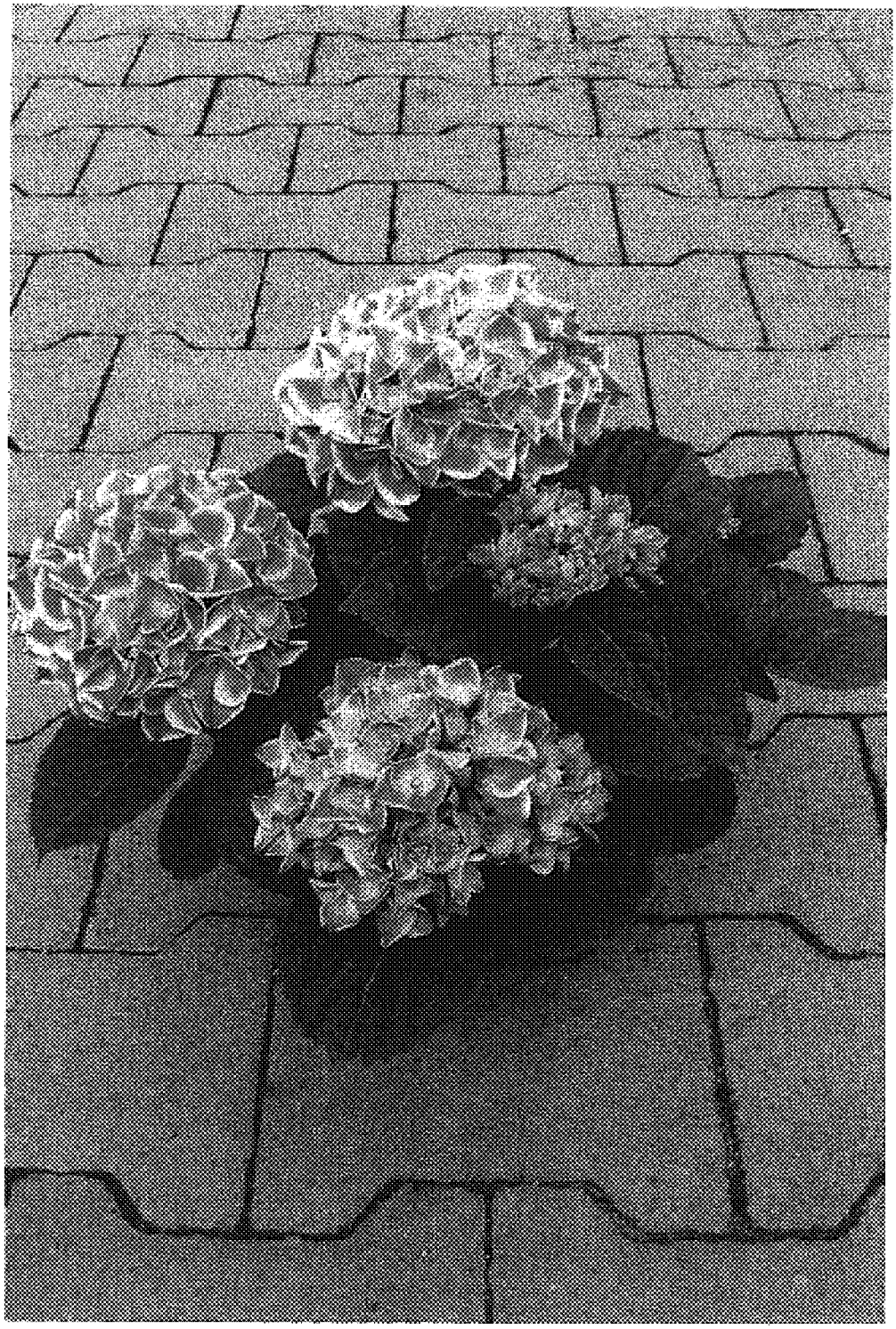
FIG. 1 is photograph of an entire plant of the new variety.

The following detailed description sets forth characteristics of the new cultivar. The plants were grown in 13 cm. pots in peat substrate at a pH of 6.0 and were 10 months past propagation when described. Measurements and color readings of the plants were taken in Dresden, Germany under natural light with a shadow present. Color references are primarily to the R.H.S. Colour Chart of the Royal Horticultural Society of London.

PLANT

Time to initiate roots: About 15 days at 18° C.
Time to develop roots: About 20 days at 18° C.
Rooting habit: Strong and adventitious root system.
Time to produce a finished flowering plant from a rooted cutting: About 42 weeks in a 13 cm. container.
Form: Symmetrical.
Height (from media surface to top of foliage): 18.0 cm.
Height (from media surface to top of flowers): 27.0 cm.
Plant diameter: 40.0 cm.
Vigor: Strong.
Strength: No artificial support needed.
Branching habit: Well-branched.
Trunk:
- *Main trunk length.*—1.0 cm.
- *Diameter.*—1.5 cm.
- *Color.*—199B.
- *Texture.*—Woody.
- *Pubescence.*—Absent.
- *Internode length.*—1.3 cm.

Lateral branches:
- *Length.*—Young: 12.0 cm. Mature: 6.0 cm.
- *Diameter.*—Young: 0.7 cm. Mature: 1.0 cm.
- *Internode length.*—2.6 cm.
- *Texture.*—Smooth with dark lenticels.
- *Pubescence.*—Absent.
- *Color.*—Young: 144A. Mature: 199B.
- *Lenticel color.*—177A.

Foliage:
- *Arrangement.*—Opposite disposition.
- *Size of leaf.*—Length: 9.6 cm. Width: 7.6 cm.

*Shape of leaf* (*generally*).—Young: Ovate. Mature: Ovate.
*Shape of apex.*—Cuspidate.
*Shape of base.*—Obtuse.
*Texture.*—Matte.
*Aspect.*—Slightly undulate.
*Margin type.*—Serrate.
*Pubescence.*—None present.
*Color.*—Young leaves: Upper surface: 137A. Lower surface: 138B. Mature leaves: Upper surface: 139A. Lower surface: 138A.
*Petiole.*—Shape: U-shaped. Length: 1.7 cm. Diameter: 0.3 cm. Color: 138B.
*Veins.*—Venation type: Pinnate. Color: Upper surface: 138B. Lower surface: 138C.

FLOWER

Natural flowering season: July in Dresden, Germany.
Flower habit: Early blooming after 10 weeks of forcing.
Bud:
*Stage of development when described.*—At full colouration.
*Shape of cluster.*—Round.
*Diameter of cluster.*—7.0 cm.
*Number of buds per cluster.*—6 fertile, 17 sterile.
*Shape.*—Fertile: Round. Sterile: Round.
*Length.*—Fertile: 0.4 cm. Sterile: 0.2 cm.
*Width.*—Fertile: 0.4 cm. Sterile: 0.2 cm.
Inflorescence:
*Shape.*—Mophead.
*Length.*—8.0 cm.
*Diameter.*—16.0 cm.
*Average number of flowers per inflorescence.*—80.
*Average number of inflorescence per plant.*—6.
*Lastingess.*—Fertile: Three weeks. Sterile: Four weeks.
Petals:
*Number per flower.*—4 to 5.
*Color.*—Upper surface: 63B. Lower surface: 63B.
*Shape.*—Round.
*Length.*—0.3 cm.
*Width.*—0.15 cm.
*Apex.*—Pointy.
*Base.*—Obtuse.
*Margin.*—Entire.
*Texture.*—Smooth.
*Tonality from a distance.*—Mixed colour.
Sepals:
*Number per flower.*—4 to 5.
*Color.*—138B.
*Shape.*—Ovate.
*Length.*—0.1 cm.
*Width.*—0.1 cm.
*Apex.*—Pointy.
*Base.*—Obtuse.
*Margin.*—Entire.
*Texture.*—Smooth.
*Fused.*—Yes.
Petaloids:
*Quantity.*—3 to 5.
*Shape.*—Ovate.
*Color.*—Upper surface: Margin: 62D. Middle: 63B. Lower surface: Margin: 62D. Middle: 62A.
Pedicels:
*Length.*—Fertile: 0.7 cm. Sterile: 2.0 cm.
*Diameter.*—Fertile: 0.1 cm. Sterile: 0.2 cm.
*Color.*—63C.
Peduncles:
*Length.*—2.5 cm.
*Diameter.*—0.3 cm.
*Texture.*—Smooth with dark lenticels.
*Color.*—138B, 178A lenticels.
Stamens:
*Number per fertile flower.*—7 to 9.
*Filament.*—Length: 0.2 cm. Color: 64A.
*Anthers.*—Shape: Round to elongated. Length: 0.1 cm. Color: 130D, but brighter.
*Pollen.*—Color: 130D, but brighter. Amount: Plentiful.
Pistils:
*Number.*—1, divided into 3 parts.
*Length.*—0.1 cm.
*Style.*—Length: 0.1 cm. Color: 138B.
*Stigma* (*divided into* 3 *parts*).—Color: 63B. Diameter: 0.15 cm.
*Ovaries* (*inferior*).—Length: 0.3 cm. Width: 0.2 cm. Color: 1D.
Fragrance: Fresh and "green".
Disease resistance: Tolerant to botrytis and powdery mildew.
Temperature tolerance: Medium, not fully winterhardy flower buds in Germany.
Drought tolerance: Medium.

I claim:

1. A new and distinct variety of *Hydrangea* plant substantially as shown and described herein.

* * * * *